United States Patent [19]

Mayr

[11] Patent Number: 6,162,600

[45] Date of Patent: Dec. 19, 2000

[54] INDICATIONS FOR THE USE AS MEDICAMENTS OF MULTIPOTENT PARAPOX IMMUNITY INDUCERS FROM ATTENUATED, NON-IMMUNOGENIC POX VIRUSES OR PARAPOX VIRUSES

[76] Inventor: Anton Mayr, Weilheimer Str. 1, D 82319 Starnberg, Germany

[21] Appl. No.: 09/171,269

[22] Filed: Oct. 14, 1998

[30] Foreign Application Priority Data

Apr. 15, 1996 [DE] Germany ............... 196 14 810

[51] Int. Cl.[7] .............. C12Q 1/70; A61K 39/245; A61K 45/00; A01N 63/00
[52] U.S. Cl. ............. 435/5; 424/232.1; 424/278.1; 424/281.1; 424/93.1
[58] Field of Search ............. 435/5; 424/232.1, 424/278.1, 281.1, 93.1

[56] References Cited

FOREIGN PATENT DOCUMENTS 35 04 940 A1  10/1985  Germany .
44 05 841 C1  1/1995   Germany .

OTHER PUBLICATIONS

Barbara Mayr, Anton Mayr, "Zum derzeitigen Stand der präklinischen Forschung über die Wirksamkeit und Unschädlichkeit von Paramunitätsinducern aus Pockenviren," Tierärztl. Prax., vol. 23, (1995), pp. 542–552, F.K. Schaltauer Verlagsgesellschaft mbH, Stuttgart—New York.

A. Mayr, M. Buttner, S. Pawlas, V. Erfle, B. Mayr, R. Brunner, & K. Osterkorn, "Vergleichende Untersuchungen über die immunstimulierende (paramunisierende) Wirksamkeit von BCG, Levamisol, Corynebacterium parvum und Präparaten aus Pockenviren in verschiedenen in vivo –und in vitro –Testen," J. Vet. Med. B., vol. 33, (1986), pp. 321–339, Paul Parey Scientific Publishers, Berlin & Hamburg.

Barbara Mayr, Diana Hörber, "Paramunisierung FeLV–positiver Katzen—ein Bericht aus der Praxis*)," Kleintierpraxis, vol. 37 (1992), pp. 515–518.

N. Breiter, F.R., Ungemach, G. Beck, D. Hegner, and A. Mayr, "Untersuchungen über die Wirksamkeit der Paramunitätsinducer PIND–AVI und PIND–ORF als Strahlenschutzsubstanzen," Strahlentherapie, vol. 161 (1985), pp. 168–176.

*Primary Examiner*—Hankyel T. Park
*Attorney, Agent, or Firm*—Barnes & Thornburg; Alice O. Martin

[57] ABSTRACT

The use is disclosed of multipotent parapox immunity inducers from attenuated, non-immunogenic pox or parapox viruses (pox inducers) to produce medicaments with new indication ranges in human medicine.

14 Claims, No Drawings

INDICATIONS FOR THE USE AS MEDICAMENTS OF MULTIPOTENT PARAPOX IMMUNITY INDUCERS FROM ATTENUATED, NON-IMMUNOGENIC POX VIRUSES OR PARAPOX VIRUSES

BACKGROUND OF THE INVENTION

The present invention relates to the use of multipotent parapox immunity inducers (pox inducers) prepared from pox and parapox viruses and the components thereof, individually or in combination, in the preparation of medicaments for novel fields of indications and therapies for which up to now no effective and most importantly no harmless medicaments are available.

SUMMARY OF THE INVENTION

Preferably, preparations derived from attenuated, non-reproductive and non-immunogenic pox and parapox viruses (also referred to as "pox inducers") intervene in the unspecific or paraspecific, respectively, phylogenetically older part of the complex immune system (natural immune system, innate immune system, primitive immune system) in a regulative, reparative and restorative manner. In the following, these pox inducers are therefore also referred to as "bioregulants". On a cellular level, the pox inducers activate macrophages, modulate NK cells and other lymphoreticular cells, while on a humoral level they control the formation of various cytokins, such as interleukin 1 $\alpha$, interleukins 2, 6, and 12, tumor necrosis factor, CSA, or of interferons (cytokin release). An introduction into the treatment of animals with pox inducers and a review of the respective experimental results is presented in B. Mayr and A. Mayr: "Zum derzeitigen Stand der präklinischen Forschung über die Wirksamkeit und Unschädlichkeit von Paramunitätsinducern aus Pockenviren. Eine Literaturstudie", Tierärztl. Praxis, vol. 23 (1995) 542–552. This novel prophylactic and therapeutical concept has been well-tried in veterinary medicine.

Important and novel in the context of the present invention is the surprising finding that the cytokins released by pox inducers promote the formation of T helper cells subtype 1 (Th1) thereby—as known from the literature—blocking the formation of subtype 2 (Th2). In fact, Th2 cells control the humoral immune response which via mast cells for the production of IgE is capable of inducing immediate type allergic reactions (antibody-dependent allergy). Thus, according to the invention Th1 cells as the antagonists of Th2 cells may prevent immediate allergies or alleviate already existing immediate-type allergies, respectively. Th1 cells act together with cellular pathogen-unspecific as well as pathogen-specific cells of the immune system and are associated (interact) with the cytokins interleukin 1 and 2, interferons, CSF and TNF, i.e. the cytokins released by the treatment with pox inducers. Therefore, there is no risk of inducing IgE-dependent allergies.

As regards their effectivity and harmlessness, pox inducers have been well-tried since in human as well as in veterinary medicine. The processes for their preparation and their use as medicaments in the prophylaxis and therapy of certain diseases have been demonstrated in DE-C-44 05 841.

The preparation of pox inducers is performed according to the processes described in DE-C-44 05 841. The starting viruses necessary for the production of pox inducers are generally obtained by amplifying the attenuated pox and parapox virus strains in cell cultures, preferably in the VERO cell line or in primary or secondary chicken embryonic fibroblast cell cultures. Only virus harvests having a titer of infectiousness of $>10^{7.0}$ KID$_{50}$/ml are used. The virus harvests of attenuated pox strains are inactivated by physico-chemical techniques, e.g. by at least 0.05% of $\beta$-propiolactone, based on the pox strain used. Following a purification by centrifugation at 4,000 g for 30 minutes (or other physico-chemical methods) the pox inducer is added with a stabilizer, such as a carbohydrate, a multivalent sugar, a protein, preferably gelatin (Polygeline (TM)) in an amount of 2.5%, based on the pox strain used. The resulting preparation is divided into portions, lyophilized, and stored at +4° C. The preparation of the ready-for-use medicament is carried out by dissolving the lyophilisate in sterile aqua dest. as described in DE-C-44 05 841. A single dose corresponds to 1 ml of dissolved lyophilisate and should contain at least 640, preferably at least 1280 VSV effective units.

As described in DE-C-44 05 841, complete virus particles but also structural elements of individual virus strains may be used in the preparation of pox inducers, e.g. fusion proteins, adsorption proteins or the 39 KD protein of parapox viruses, as well as so-called "empty capsids" of pox viruses. In these cases an inactivation step is no longer necessary.

A detailed description of the individual preparative steps and possibilities of pox inducers from combinations of several pox or parapox virus strains, respectively, may be found in DE-C-44 05 841 which is explicitly incorporated herein by reference.

Regarding the use as a medicament we were not only able to confirm the indications for pox inducers from combinations of pox viruses according to the invention listed in the present patent document but, surprisingly, with respect to prophylaxis and therapy have discovered completely novel possibilities of use for the pox inducers for which up to now medicaments for parenteral or oral administration have not been available which are effective and at the same time probably harmless also in the case of long-term application or overdosage.

Accordingly, in extension of the teaching of DE-C-44 05 841 the present invention relates to novel indications for use of the pox inducers on the basis of pox and parapox viruses in the prophylaxis and therapy of diseases in humans. These novel indications are based on the surprising finding that these pox inducers are capable of regulating a disturbed immune system into the optimal physiological range not only with respect to an increase or a stimulation, respectively, of reduced or suppressed activitities but also with respect to a decrease of pathologically elevated immune parameters. To understand the regulatory effect of pox inducers in the sense of a bioregulation occuring in an association between the immune system, the hormonal system and the neural system one has to realize that the individual humoral as well as cellular activitites of the immune system affect and control each other in a stimulatory as well as a suppressing manner. i.e., if cellular as well as humoral (soluble) components of the complex immune system are induced by means of pox inducers a self-regulating system develops in the organism. For example, this may occur by an increase or decrease, respectively, of the number or activity of specific effector cells (e.g. macrophages, leucocytes, T cells, NK cells) or an increase or decrease in the production of cellular or humoral communication molecules (e.g. IL 1 or 2, interferons etc.). In these instances every organism will show a different individual reaction depending on the functional state of its defense system at the start of the therapy with pox inducers. Thus, the term "bioregulation" by pox inducers as used herein is meant in a much broader sense as is generally encompassed in the understanding of a so-called "immunotherapy". Thus, for example in a patient after a treatment with pox inducers the number of leucocytes may increase and, conversely, the number of NK cells may maintain their level of activity or may be reduced. Therefore, to balance dysregulations of the immune system it is not necessary for all of the immunological parameters to be stimulated or suppressed at the same time because only existing deficiencies or excessive values will be equalized. For this reason, the individualization into the normal physiological range by a treatment with pox inducers is a completely novel finding. Since at the same time an intervention of pox inducers in the individual defense system will also have a regulatory effect on the neural and humoral systems, pox inducers should not be defined as immunoregulants but instead it is suggested to consider them as bioregulants. Up to now a bioregulant of the type described has not been available in medicine which is harmless also in the case of severe overdosage, does not affect the "normal physiological values" of the immune system, and in the case of a dysfunction acts in a regulatory manner in the sense of a physiological normalization, which means stabilized or restored, respectively, in its overall functionality. Thus, pox inducers are excellently useful in prophylactic as well as metaphylactic applications to patients suffering from a dysregulated immune system, e.g. in the case of immune deficiencies of different genesis such as after an immunosuppressive therapy, immunosuppressive basic conditions or by exogenous influences such as stress situations, extraordinary burdens, long travels, acute infection events in the surroundings. For a prophylactic parapox immunization usually 2 to 3 injections of a pox inducer preparation given on successive days immediately prior to an expected strain situation will be sufficient. Metaphylactic or therapeutic administrations of pox inducers should be carried out at least for 3 days or until the clinical symptoms clearly subside. Following severe disease conditions and mainly after getting over infectious diseases convalescence should be supported by 2 to 3 injections per week of a pox inducer preparation until complete recovery is achieved.

Furthermore, the invention is based on the surprising finding that pox inducers individually or in combination are useful as adjuvant, accompanying therapeutics in the reduction or prevention, respectively, of unwanted damages associated with chemotherapy or radiotherapy in the fighting of tumors or prevention of metastases, respectively. According to present experiences in those cases the treatment using pox inducers is performed in different phases. At the beginning the patient receives 5 to 10 times each a 1 ml injection (i.m.) of at least the 640 VSV effective units on successive days. In the following, 2 to 3 injections per week are administered for at least 3 weeks while later 1 injection per week will be administered. For tumor patients who are negative for all clinical and immunological tests the further treatment may be reduced to 2 injections per month. Cases which are not totally unambiguous should be given one injection per week for a prolonged period (weeks or months).

A further surprising possibility of use of the pox inducers individually or in combination is their employment in prefinal tumor therapy, such as in the case of tumorous diseases which are inoperable and where a treatment is no longer possible, to alleviate unbearable pain and to improve the well-being and thus the life quality of the patients. In such cases the pox inducers are administered at least twice a week or otherwise daily depending on the subjective feeling of the patient. This treatment is compatible with the presently used analgetics such as morphine. It even results in a reduction up to a discontinuation of the previous application of analgetics.

Furthermore, the invention is based on the observation that surprisingly a long-term therapy with pox inducers in HIV patients contributes to an improvement of the immunological state in part leading to a reduction of the HIV antigen content in the blood. Reports uniformly state an optimization of the well-being, an improvement in performance and a positive view towards getting over the disease. Opportunistic secondary infections are prevented or quickly brought to an end without postinfectious complications, such as herpes simplex, herpes zoster, pseudomonas infections, influenza infections. The mode of treatment equals that of the tumor patients. Also HIV-positive patients should be given pox inducers (if possible once a week) for their whole life-time in order to maintain an optimal defense of infections. If infections occur the intensive daily treatment with pox inducers is immediately commenced which will be only reduced if a clear clinical improvement is observed.

Another use according to the invention is the long-term accompanying therapy of multiple sclerosis to alleviate the phases of the disease and to prolong the intervals between two phases. The treatment is effected as in the case of tumor patients. Also this treatment must be continued for the whole life-time. Up to now experiences in the treatment of children and elderly patients with pox inducers individually or in combination are available.

Moreover, the invention relates to the use of pox inducers individually or in combination in operation prophylaxis to reduce or to prevent, respectively, hospital infections and to optimize wound healing. Preferably, the treatment is started 3 to 5 days prior to operation and is continued up to at least 3 days following the operation. An intramuscular administration is most favourable, but also an intranasal application of the undissolved lyophilisate (i.e. the powder) into the nasal cavity may be performed.

Surprisingly, the treatment with pox inducers is also useful in substitution therapy (such as antibiotics) in the case of poor or absence of healing of wounds or skin sores if a conventional therapy fails. Typical examples for poorly healing wounds or skin sores are ulcus cruris, panaritium, and chronic open eczemas. In such cases besides parenteral application the local treatment across the concerned skin areas with appropriate preparations, e.g. powders, ointments, cremes, lotions, with the pH adjusted to about 7 to 8, has shown to be particularly useful. In such cases the patients receive an inducer injection daily until the wound has closed. A continuous local application using appropriate ointments, such as Bepanthen (TM), addionally promotes healing.

The pox inducers on the basis of pox and parapox viruses used according to the invention for the novel indications are well-tolerated and harmless also in the case of overdosage and long-term treatment. Up to now a prophylactic or therapeutic, respectively, for parenteral application complying with these criteria is unknown. The harmlessness of a treatment is considered to be the most important criterion in medicine. To date a prophylactic or therapeutic, respectively, that exhibits sufficient effectivity to be useful in the fields of indications according to the invention mentioned is not yet available.

The known so-called immunomodulators used at present, such as BCG, levamisole, C. parvum and Freund's adjuvant, on the one hand are not harmless and on the other hand are effective only in one direction, i.e. either stimulatory (stimulants, adjuvants etc.) or suppressive (immunosuppression). A medicament combining both properties while achieving optimal physiological parameters in the sense of the bioregulants defined herein is not available up to now. In addition, to date, for the other clinical areas of application or indications, respecitively, according to the invention, such as substituting tumor therapy, fighting of pain in the prefinal stage, treatment of AIDS in HIV-positive patients, long-term treatment of multiple sclerosis, support of wound healing, comparable harmless and effective medicaments are unknown.

EXAMPLES

The application of the pox inducers used according to the invention for the indications described herein may be parenteral or local, e.g. intranasal, in the form of an aerosole spray, oral, rectal or vaginal. Preferably, the pox inducers are administered by the intramuscular mode. The manufacture of drug preparations is carried out in conventional manner. However, it is necessary to adjust the pH of the preparations to about 7 to 8.

The following Examples are presented to further illustrate the invention.

The pox inducers as described herein are combination preparations on the basis of pox or parapox viruses, respectively, which in the following are referred to as "Conpind" (TM applied). The content per dose is 1280 VSV effective units. One dose is dissolved in 1 ml of aqua dest.

Example 1

Since April, 1994, 17 patients in total were treated in an immunological doctor's surgery 6 times each by intramuscular administration of 1 ml of Conpind in an interval of 3 to 5 days. Prior to the start and after the end of the treatment the clinical and immunological data were obtained and reported. The individuals concerned were patients suffering from an increased proneness to infections of different genesis which had led to various severe clinical diseases such as recurrent erysipelas, recurrent herpes infections, colitis, sinusitis as well as allergies. The intramuscular injections were very well tolerated; no local or systemic side effects were observed. A clear improvement of the general condition even after a short treatment interval was observed in all of the 17 patients. An increased appetite partly accompanied by weight gain as well as a positive effect on the mood were observed as positive side effects. All of the patients were followed up for at least 1 year. Within this period no new infections occurred in 10 of the patients while the proneness to infections was clearly reduced for the remaining 7 patients.

In contrast to this very positive and uniform findings with respect to the clinical evaluation of the treatment with Conpind the behavior of the immunological parameters exhibited great individual differences. Pathologically increased values generally decreased in the course of the relatively short treatment interval of a maximum of 3 weeks while deficitary values increased. In contrast, immunological parameters which had been in a normal range prior to the start of the treatment remained unchanged. Therefore, they have not been listed separately in the following Table I. Table I exemplarily shows a list of typical immunological parameters of 3 patients. Studying the Table it will be recognized that in a single patient of the different values some have increased while others have decreased. Interestingly and surprisingly, even a 82-year-old female patient showed a positive response to the treatment.

TABLE I

Bioregulatory effect of Conpind in 3 patients with immunological deficiencies

| Patient | Indication | Parameter | Normal range | Prior to CP | After CP | Evaluation |
|---|---|---|---|---|---|---|
| Pat. 2 (m.) 25 years | Neurodermitis, allergy, alopecia | Leucocytes | 4000–10000 | 6700 | 4600 | ↓ |
| | | Lymphocytes | 20–30% | 38% | 32% | ↓ |
| | | T cells | 60–80% | 62% | 71% | ↑ |
| | | act. T cells | 0–12% | 3% | 7% | ↑ |
| | | B cells | 7–23% | 27% | 20% | ↓ |
| Pat. 6 (f.) 54 years | Colitis ulcerosa | Lymphocytes | 20–30% | 10% | 18% | ↑ |
| | | T cells | 60–85% | 69% | 73% | ↑ |
| | | IL-2/CD4 cells | 15–40% | 12% | 17% | ↑ |
| Pat. 14 (m.) 38 years | system. immuno-deficiency, allergy | Leucocytes | 4000–10000 | 4100 | 7000 | ↑ |
| | | Lymphocytes | 20–30% | 35% | 28% | ↓ |
| | | Ts cells | 19–48% | 32% | 42% | ↑ |
| | | IL-2/CD4 cells | 15–40% | 16% | 21% | ↑ |
| Pat. 12 (f.) 82 years | Polyarthritis, reactive depression | Lymphocytes | 20–30% | 11% | 15% | ↑ |
| | | CD4/CD8 r. | 0.8–2.8 | 0.9 | 1.4 | ↑ |
| | | Ts cells | 19–48% | 41% | 27% | ↓ |

Example 2

15 patients suffering from severe viral infections or viral infections where a treatment was no longer possible, respectively, were treated in a clinic with Conpind. The treatment was performed on a daily basis with one intramuscular Conpind dose until a clear improvement of the clinical symptoms was observed. Subsequently and until complete recovery, the patients received one Conpind dose per week. The 15 patients suffered from various herpes infections (h. simplex, h. genitalis, zoster), hepatitis B as well as recurrent viral infections of different genesis. As becomes clear from Table II also in this patient group individual immunological parameters in a single patient were shown to increase while others decreased. Generally the number of those patients was higher whose leucocyte and lymphocyte counts increased albeit only slightly. Also the CD4/CD8 ratio as well as Th cells increased significantly on average. In contrast no significant change was observed in the number of Ts cells.

TABLE II

Bioregulatory effect of Conpind in 15 patients with viral infections

Effect of Conpind on immunological parameters

| Patient | Indication | Parameter | Normal range | Prior to CP | After CP | Evaluation |
|---|---|---|---|---|---|---|
| Pat. 1 (m.) 43 years | Recurrent viral infections | Leucocytes Lymphocytes CD4/CD8 r. | 4000–10000 0.8–2.8 | 13300 11438 0.66 | 14700 11466 1.55 | ↑ — ↑ |
| Pat. 2 (m.) 57 years | herpes zoster | Leucocytes Lymphocytes CD4/CD8 r. | 4000–10000 0.8–2.8 | 6800 1836 0.83 | 10000 4200 1.28 | ↑ ↑ ↑ |
| Pat. 5 (m.) 54 years | herpes genitalis | Leucocytes Lymphocytes CD4/CD8 r. | 4000–10000 0.8–2.8 | 5800 2784 1.63 | 5800 2784 1.53 | — — ↓ |
| Pat. 8 (f.) 27 years | herpes genitalis | Leucocytes Lymphocytes CD4/CD8 r. | 4000–10000 0.8–2.8 | 7700 2079 0.68 | 8100 2916 1.11 | ↑ ↑ ↑ |
| Pat. 13 (f.) 37 years | herpes genitalis | Leucocytes Lymphocytes CD4/CD8 r. | 4000–10000 0.8–2.8 | 7700 2772 1.09 | 10700 2782 1.24 | ↑ — ↑ |
| Pat. 15 | herpes zoster | Leucoyytes Lymphocytes CD4/CD8 r. | 4000–10000 0.8–2.8 | 6900 2691 1.43 | 5500 1485 1.24 | ↓ ↓ ↓ |

Example 3

Fifteen patients suffering from different tumors were treated in an immunological doctor's surgery according to the same schedule as in Example 1 (6 doses of Conpind in an interval of 3 to 5 days). Four of the patients came into the surgery after successful operation and completed radiation treatment, 3 after resection of the tumor and 8 after a chemotherapy. The immunological state of the patients was examined prior to the start of treatment as well as following the last treatment. All of the patients were followed up for at least 1 year. The treatment was very well tolerated by all of the patients. No local or systemic side reactions were observed. In all of the patients the general condition was improved and, in addition, the treatment by Conpind had a positive effect on the appetite and mood of the patients. In some of the patients the tumors became smaller. No metastases occured in the follow-up period of 1 year.

The Tables III to V summarize the effect of the treatment of the tumor patients with Conpind on immunological parameters with respect to individual cases. Values which were in the normal range prior to the start of the treatment and remained unchanged have been omitted. In this respect it is surprising that also in these patients individual parameters were increased while others were decreased. While these changes often occurred within the normal range they clearly indicated a positive response of the patient to the treatment. Furthermore, it is interesting that even very old patients such as the female patient No. 27 at an age of 93 showed a positive response to the treatment. It is still unknown which functional mechanisms are the basis of the mutual reactions between the individual parameters. However, it has been proven that following a Conpind treatment the individual parameters change towards physiological normalization in different ways and that in any case this bioregulation leads to a benefit for the health of the patient.

TABLE III

Bioregulatory effect of Conpind on the immunological state of tumor patients following operation and radiotherapy Effect of Conpind on immunological parameters

| Patient | Indication | Type | Normal range | Prior to CP | After CP | Evaluation |
|---|---|---|---|---|---|---|
| Pat. 24 (m.) 58 years | Colon ca. radiation-induced immune suppr. | Leucocytes Th cells Ts cells NK cells | 4000–10000 29–59% 19–48% 6–29% | 3800 29% 33% 42% | 4600 35% 43% 32% | ↑ ↑ ↑ ↓ |
| Pat. 21 (m.) 43 years | Metastazing parotis ca. | Leucocytes NK cells IL-2/CD4 cells | 4000–10000 6–29% 15–40% | 3800 34% 22% | 9900 9% 31% | ↑ ↓ ↑ |
| Pat. 30 (f.) 54 years | Mamma ca. | Leucocytes CD4/CD8 r. Th cells act. T cells IL-2/CD4 cells | 4000–10000 0.8–2.8 29–59% 0–12% 15–40% | 4200 2.3 51% 13% 38% | 5500 2.6 57% 7% 15% | ↑ ↑ ↑ ↓ ↓ |

TABLE IV

Bioregulatory effect of Conpind on the immunological state of tumor patients following resection of the tumor Effect of Conpind on immunological state

| Patient | Indication | Type | Normal range | Prior to CP | After CP | Evaluation |
|---|---|---|---|---|---|---|
| Pat. 22 (m.) 58 years | Colon ca. | Leucocytes | 4000–10000 | 4300 | 7800 | ↑ |
| | | T cells | 60–85% | 55% | 65% | ↑ |
| | | CD4/CD8 r. | 0.8–2.8 | 0.8 | 1.4 | ↑ |
| | | Th cells | 29–59% | 35% | 49% | ↑ |
| | | Ts cells | 19–48% | 46% | 35% | ↓ |
| | | NK cells | 6–29% | 38% | 26% | ↓ |
| Pat. 28 (f.) 58 years | Colon ca. | Leucocytes | 4000–10000 | 3600 | 5200 | ↑ |
| | | Th/Ts ratio | 0.8–2.8 | 0.8 | 1.9 | ↑ |
| | | Ts cells | 19–48% | 42% | 33% | ↓ |

TABLE V

Bioregulatory effect of Conpind on the immunological state of tumor patients following chemotherapy Effect of Conpind on immunological parameters

| Patient | Indication | Type | Normal range | Prior to CP | After CP | Evaluation |
|---|---|---|---|---|---|---|
| Pat. 19 (f.) 59 years | Lung ca. | Lymphocytes | 20–30% | 8% | 11% | ↑ |
| | | act. T cells | 0–12% | 17% | 12% | ↓ |
| | | NK cells | 6–29% | 8% | 32% | ↑ |
| | | IL–2/CD4 cells | 15–40% | 60% | 28% | ↓ |
| Pat. 25 (f.) 44 years | Malignant melanoma | Leucocytes | 4000–10000 | 9400 | 6700 | ↓ |
| | | Lymphocytes | 20–30% | 16% | 24% | ↑ |
| | | CD4/CD8 r. | 0.8–2.8 | 2.4 | 1.8 | ↓ |
| | | Th cells | 29–59% | 48% | 53% | ↑ |
| | | Ts cells | 19–48% | 20% | 26% | ↑ |
| | | NK cells | 6–29% | 15% | 11% | ↓ |
| | | IL-2/CD4 cells | 15–40% | 20% | 24% | ↑ |
| Pat. 27 (f.) 93 years | Recurrent basalioma | Leucocytes | 4000–10000 | 6400 | 8900 | ↑ |
| | | T cells | 60–85% | 90% | 80% | ↓ |
| | | CD4/CD8 r. | 0.8–2.8 | 0.8 | 1.4 | ↑ |
| | | IL-2/CD4 cells | 15–40% | 12% | 21% | ↑ |

Example 4

The effect of a continuous treatment with Conpind on the development of harmful side reactions during or after radiotherapy or chemotherapy has been examined in 7 tumor patients. Four of these patients had undergone resection of the primary tumor while three of the patients had not been subjected to surgery because of the presence of metastases. All of the 7 patients received chemotherapy e.g. with cisplatin or endoxan. In addition 2 of the patients with operation and 1 patient without operation underwent radiotherapy. All of the patients received 1 daily dose of Conpind as well as 1 dose of Conpind each 2 to 3 times per week in the treatment intervals from the beginning of the radiotherapy or chemotherapy. None of the patients (2 male, 5 female) encountered the feared damages caused by chemotherapy or irradiation. The patients had a sense of well-being and were positively motivated. The Conpind treatment was continued after the end of chemotherapy or radiotherapy: In the following 5 weeks 1 dose of Conpind on each of 2 days per week, then 2 intramuscular doses of Conpind per month. Up to now the Conpind patients are in the best of health (parapox immunization started 3½ or 2 years ago, respectively). According to retrospective studies, comparable patients during or after chemotherapy or radiotherapy encountered the well known severe organic and psychical injuries.

Example 5

In the case of 5 patients with inoperable and finally treated tumor diseases which despite of an appropriate pain-relieving treatment were suffering from the most severe pain and depressions and therefore were at risk of suicide the benefits of the Conpind treatment were used to modulate the pain and to relieve the depression. Three of the patients were suffering from colon carcinoma which already had formed metastases systemically over the whole body. Two of the female patients suffered from mamma carcinoma with metastases in the brain, spine, lung and in other organs. Death was expected to be imminent in the case of all 5 patients. In this stage, the patients received 1 intramuscular Conpind dose daily or every 2 to 5 days, respectively, until they died. The pain was decreased already after 3 to 5 applications and in some cases completely ceased. Striking and totally surprising was the change in the patients' psyche. They lost their depressions, became optimistic with respect to their recovery and experienced a subjective sense of well-being. Two of these patients even demanded to be discharged from the hospital because they were convinced that they would recover. However all of the 5 patients died within 2 to 5 months after the start of the Conpind treatment in a condition of optimistic well-being.

In another patient suffering from generalized prostatic carcinoma who had to be treated with morphine, the morphine treatment could be immediately discontinued after the treatment with Conpind had been commenced without encountering detrimental consequences.

Example 6

Seven HIV-infected patients (5 still without symptoms, 2 with influenza symptoms at the start of Conpind treatment, 1 female patient with extensive herpes zoster) were treated with Conpind in three phases since 1 to 3 years. In the first phase, they received 1 dose of Conpind daily over 10 days. The subsequent second phase lasted 5 weeks. During this time, they were treated with 1 dose of Conpind on 2 days per week, followed by the third phase in which they received 1 dose of Conpind once to twice per month continuously up to now. All of the 7 HIV-infected patients remain asymptomatic to date and are in paid employment. The influenza symptoms of the 2 ill patients as well as of the female zoster patient disappeared already a few days after the start of the treatment. No post-zoster neuritis was experienced. For 1 patient the virus antigen content in blood was examined and was found to have decreased by more than 50% within 4 weeks. At the wish of the HIV-infected patients the monthly Conpind doses were then given on a weekly basis. Under this treatment regimen the HIV-infected persons experienced a much greater sense of well-being. Their fear of the occurence of new depressions or diseases could be reduced in this manner.

Example 7

Experiences with respect to the positive effects of a long-term accompanying therapy are available for 5 multiple sclerosis patients. The patients are 25 years (2 cases, female) to 72 years (1 case, male) of age. The remaining 2 patients (male) are between 50 and 60 years old. The Conpind treatment was started 3 years ago and continued up to now. The patients received 1 dose of Conpind on 2 days each per week. All of the 5 patients report a very good tolerability, a positive effect on the psyche, an increasing prolongation of the intervals between new MS phases as well as a milder course of new phases. A sixth female patient (13 years old) suffering from multiple sclerosis since 2 years but still able to walk was treated by intramuscular administration of 1 dose of Conpind because since 3 weeks she suffered from a permanently progressing faecal and urinary incontinence. After only a single treatment with Conpind a complete remission of the incontinence could be achieved within 5 hours.

Example 8

The positive effect of prophylactic and accompanying Conpind treatments could be excellently documented in the case of patients facing an operation. The prophylactic daily application of Conpind (intramuscular, nasal—undissolved lyophilisate) with or without antibiotics 2 to 3 days prior to operation has turned out to be successful in numerous operations in at least 5 clinics. The intramuscular administration of Conpind is carried out 2 to 3 times (1 dose each) on successive days. The treatment may be repeated after the operation. In total, 60 patients with most different indications for operation (bypass, ablatio mammae, exstirpatio uteri etc.) have been treated in this manner. Generally, an improved wound healing (primary healing, no complications, shortening of the healing process) was reported. No case of hospital infection was encountered.

Example 9

Twelve patients with liver damages to a different extent following diagnosed hepatitis A, B or C infections were treated since 3 years with Conpind according to Example 6. The preparation was administered by intramuscular injection. The patients report freedom from pain, an improved general condition and the ability to work. A reduction in the relevant liver parameters, e.g. γ-GT transaminases, was reported. No recurrencies occured up to now. Thus, pox inducers may be used in the regeneration of hepatocytes and in the treatment of chronic liver diseases.

Concluding evaluation of the harmlessness of pox inducers individually and in combination.

The harmlessness of the pox inducers PIND-AVI and PIND-ORF and the combination Conpind has been proven by long-term treatment in self-experiments and in the wide circle of family and friends. Between 1972 and 1982, parapox immunity inducers from pox viruses (precursor preparations of Conpind, e.g. Duphapind®, Baypamun®, PIND-AVI, PIND-ORF, Paravi) were used regularly, i.e. at least once within 2 months, to remedy a proneness to infections and for stress prophylaxis by local (oral (gargling) or nasal (sniffing)) application. A local treatment consisted of 6 to 10 applications in intervals of 4 to 24 hours.

Other persons of the circle of family and friends underwent a regular parenteral treatment with pox inducers since 1983. For this purpose, 6 to 8 courses of treatment per year with 2 to 3 injections each of 1 dose of pox inducers ad us. vet. (no combination preparation, e.g. Duphapind®, Baypamun P®) were used in prophylaxis and metaphylaxis.

Since 1993, the same group of people uses Conpind for this purpose, frequently combining local and parenteral application in the case of an acute risk of infections. Up to now, negative side reactions or allergies were not observed in any of the cases mentioned, while the effectivity was completely maintained. Besides parenteral, oral and nasal application also the local application by means of ointments was successful in the case of poor wound healing or ulcera.

What is claimed is:

1. A method for treating a person with a disregulated immune system or providing adjuvants to a treatment, such method comprising:
    (a) obtaining a medicament comprising an inducer from a combination of poxvirus that regulates a distributed immune system into a normal physiological range; and
    (b) administering an effective amount of the medicament to the person with the disregulated immune system.

2. The method of claim 1, wherein the disregulated immune system is caused by a condition selected from the group consisting of persons undergoing chemotherapy or radiotherapy to remove tumors and prevent metastasis, undergoing prefinal tumor therapy, having a disturbed immune system due to HIV, undergoing therapy for multiple sclerosis, anticipating surgery, having a wound, having a skin sore, having a viral infection, prone to infections, anticipating stress, and with a hepatitis infection.

3. The method of claim 1, wherein the medicament is applied locally or parenterally.

4. The method of claim 1, wherein the pox inducer comprises attenuated, non-immunogenic pox or parapox viruses.

5. The method of claim 4, wherein the pox or parapox viruses are inactivated.

6. A method for reducing or preventing undesired damages in a person with a tumor following chemotherapy or radiotherapy, said method comprising:
    (a) obtaining a medicament as an adjuvant accompanying the chemotherapy or radiotherapy, said medicament comprising an inducer from a combination of poxvirus that regulates a disturbed immune system into a normal physiological range; and
    (b) administering an effective amount of the medicament to the person with the tumor.

7. A method for allocating pain and optimizing the well being of a person undergoing prefinal tumor therapy, said method comprising:

(a) obtaining a medicament for a prefinal tumor therapy comprising an inducer from a combination of poxvirus that regulates a disturbed immune system into a normal physiological range; and (b) administering an effective amount of the medicament to the person undergoing prefinal tumor therapy.

8. A method for improving the immunological state in an HIV patient, said method comprising:

(a) obtaining a medicament comprising an inducer from a combination of poxvirus that regulates a disturbed immune system into a normal physiological range; and (b) administering an effective dose of the medicament to the person with HIV.

9. A method for adjuvant therapy for a person receiving therapy for multiple sclerosis, said method comprising:

(a) obtaining a medicament for the adjuvant accompanying the therapy, said medicament comprising an inducer from a combination of poxvirus that regulates a disturbed immune system into a normal physiological range; and (b) administering an effective amount of the medicament to the person receiving therapy for multiple sclerosis.

10. A method for preventing infections in a person after an operation, said method comprising:

(a) obtaining a medicament comprising an inducer from a combination of poxvirus that regulates a disturbed immune system into a normal physiological range; and (b) administering an effective amount of the medicament to the person before an operation on the person.

11. A method to optimize wound healing, said method comprising:

(a) obtaining a medicament comprising an inducer from a combination of poxvirus that regulates a disturbed immune system into a normal physiological range; and (b) administering an effective dose of the medicament to a person with a wound.

12. A method to treat a condition, said condition selected from the group consisting of viral infections, proneness to infections and anticipated stress, said method comprising:

(a) obtaining a medicament comprising an inducer from a combination of poxvirus that regulates a disturbed immune system into a normal physiological range; and (b) administering the medicament to a person with the condition.

13. A method to treat a person having liver damage resulting from a hepatitis infection, said method comprising:

(a) obtaining a medicament comprising an inducer from a combination of poxvirus that regulates a disturbed immune system into a normal physiological range; and (b) administering an effective dose of the medicament to a person with the hepatitis infection.

14. A method to reduce or prevent undesired damages resulting from chemotherapy or radiotherapy, said method comprising providing adjuvant treatment to a person undergoing chemotherapy or radiotherapy, said method comprising:

(a) obtaining a medicament for an adjuvant accompanying the therapy, said medicament comprising an inducer from a combination of poxvirus that regulates a disturbed immune system into a normal physiological range; and (b) administering an effective amount of the medicament by local or parenteral application.

* * * * *